United States Patent [19]

Wilk et al.

[11] Patent Number: 5,746,694
[45] Date of Patent: May 5, 1998

[54] ENDOSCOPE BIOPSY CHANNEL LINER AND ASSOCIATED METHOD

[76] Inventors: Peter J. Wilk, 185 West End Ave., New York, N.Y. 10023; Naomi L. Nakao, 303 E. 57th St., New York, N.Y. 10022

[21] Appl. No.: 648,906

[22] Filed: May 16, 1996

[51] Int. Cl.⁶ ........................................ A61B 1/04
[52] U.S. Cl. ........................ 600/123; 600/121; 600/153
[58] Field of Search ........................... 600/121, 122, 600/123, 124, 125, 153, 154, 155, 156

[56] References Cited

U.S. PATENT DOCUMENTS

| | | |
|---|---|---|
| 2,548,602 | 4/1951 | Greenburg . |
| 3,654,049 | 4/1972 | Ausnit . |
| 4,646,722 | 3/1987 | Silverstein et al. . |
| 4,741,326 | 5/1988 | Sidall et al. .................. 600/123 |
| 4,815,470 | 3/1989 | Curtis et al. . |
| 4,858,286 | 8/1989 | Siegel . |
| 4,886,049 | 12/1989 | Darras . |
| 4,947,827 | 8/1990 | Opie et al. . |
| 5,025,778 | 6/1991 | Silverstein et al. . |
| 5,050,585 | 9/1991 | Takahashi .................. 600/123 |
| 5,217,001 | 6/1993 | Nakao et al. . |
| 5,257,617 | 11/1993 | Takahashi .................. 600/123 |
| 5,386,818 | 2/1995 | Schneebaum et al. ........ 128/4 |

*Primary Examiner*—Beverly M. Flanagan
*Attorney, Agent, or Firm*—R. Neil Sudol; Henry D. Coleman

[57] ABSTRACT

A device utilizable with an endoscope to promote cleanliness comprises a substantially thin-walled elongate tubular sheath made of a flexible material, the sheath having a use configuration with an inner diameter larger than an outer diameter of an insertion member of the endoscope, whereby the sheath may be removably disposed about such insertion member to substantially surround same prior to insertion of the insertion member into a patient. A liner element extends parallel to the sheath and inside the sheath at least along a distal end portion of the liner element. The liner element is insertable into a biopsy channel of the insertion member of the endoscope. The sheath and the liner element are attached at their distal ends by a transparent cap member to form a germ-tight seal. Biopsy channels expandable from a collapsed configuration to receive endoscopic surgical instruments during an operation are provided in or on the sheath.

13 Claims, 7 Drawing Sheets

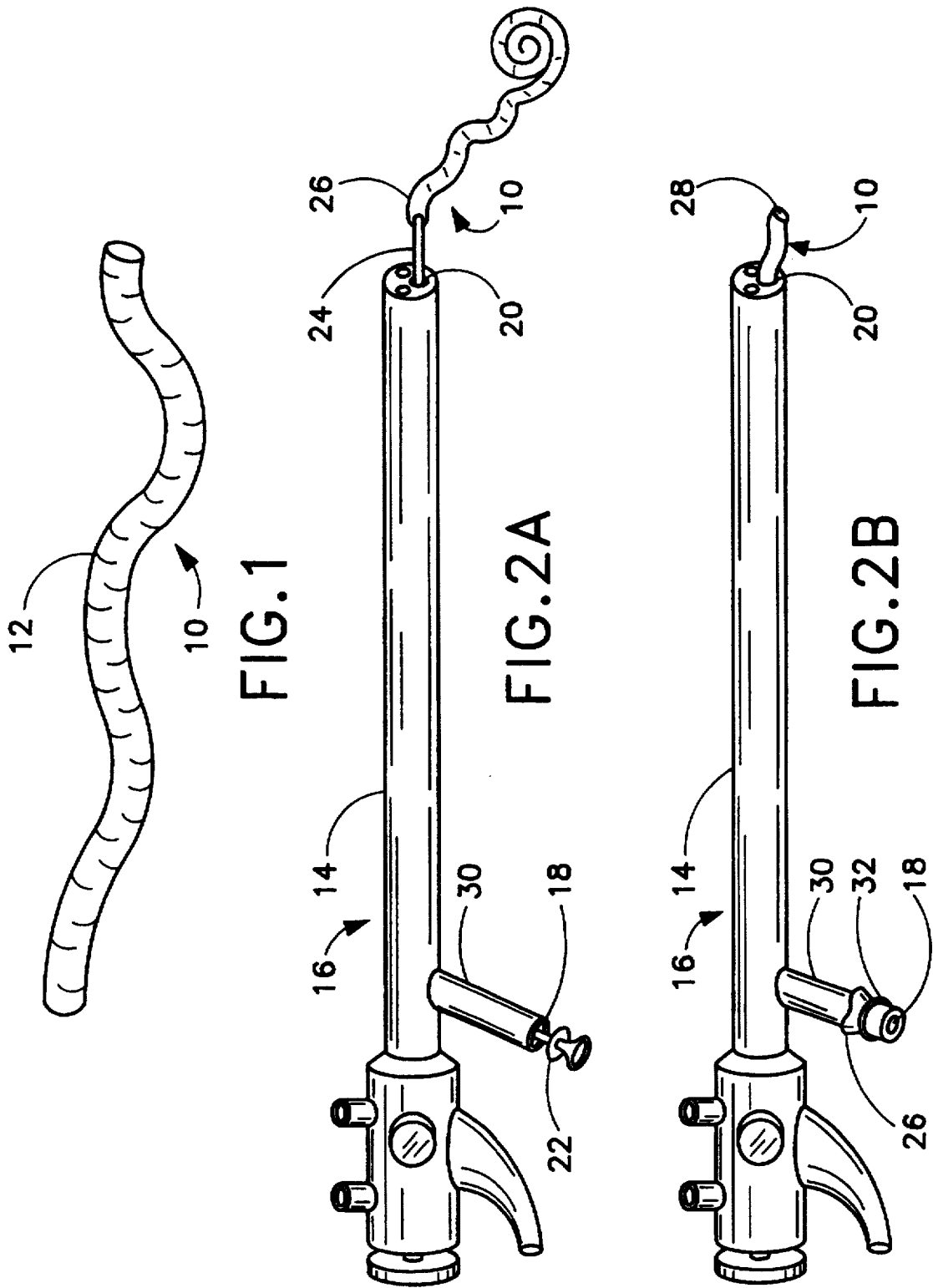

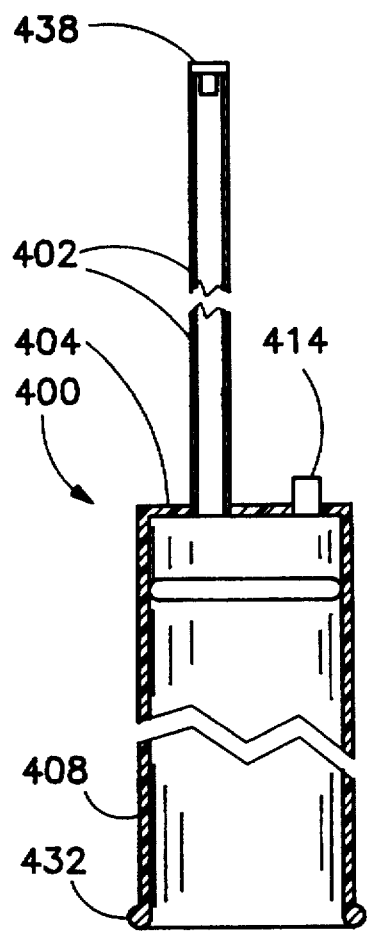
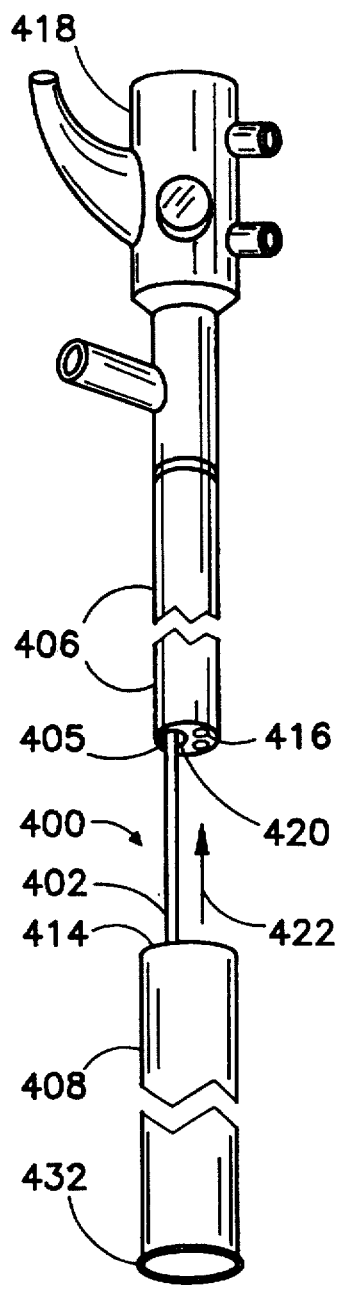
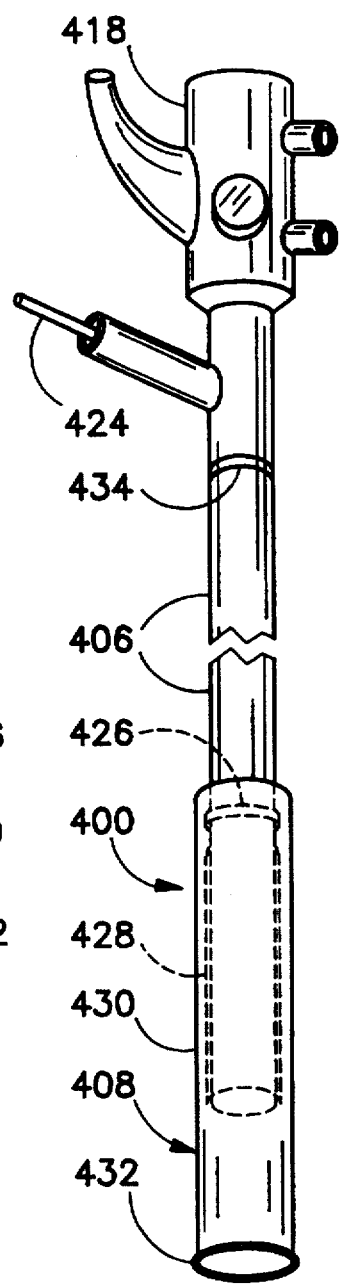
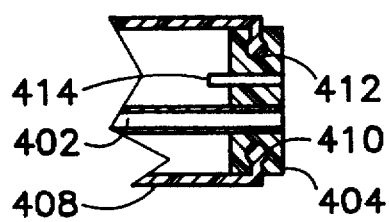
FIG. 12
FIG. 15
FIG. 13
FIG. 14

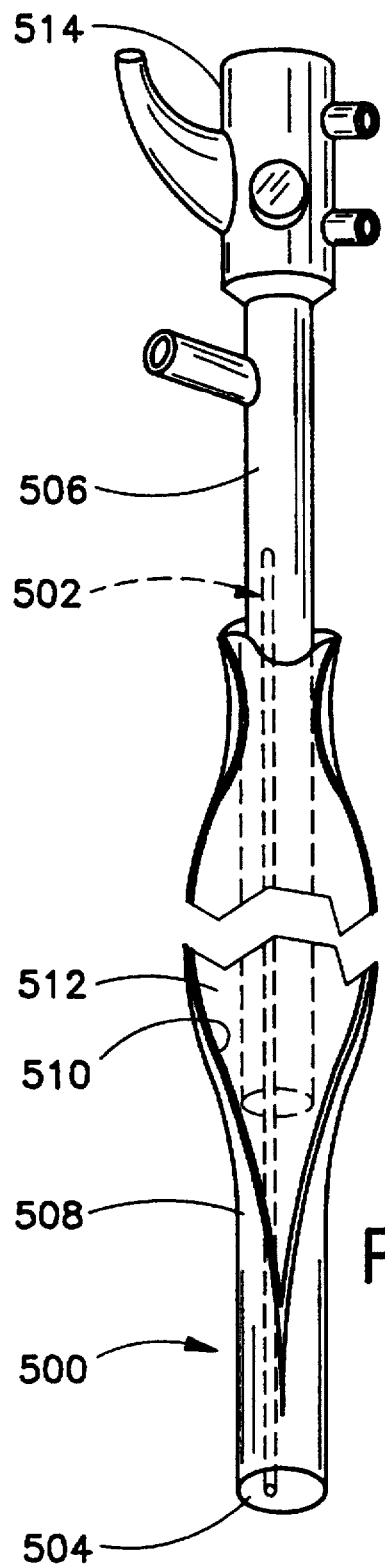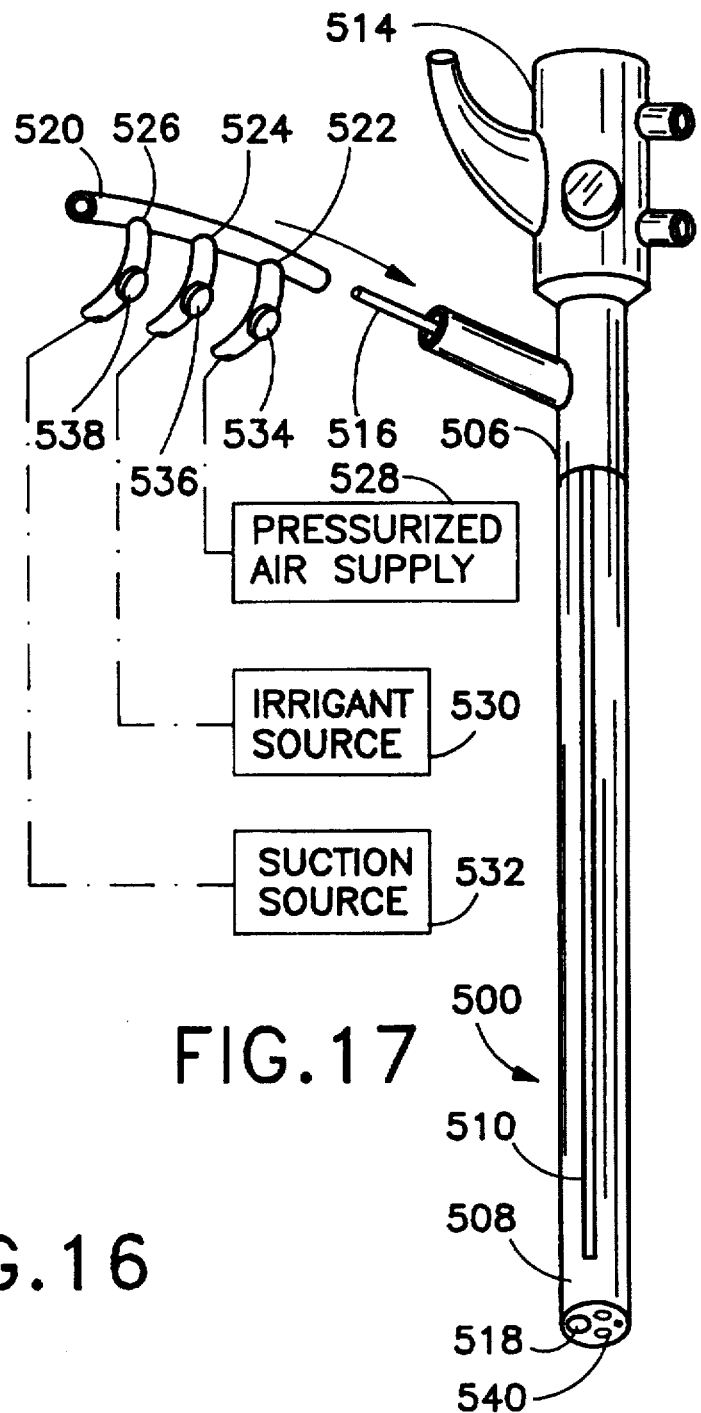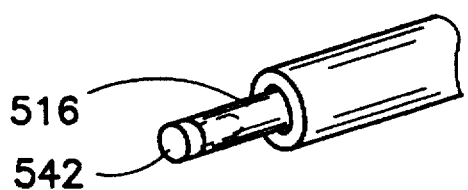
FIG. 16
FIG. 17
FIG. 18

ENDOSCOPE BIOPSY CHANNEL LINER AND ASSOCIATED METHOD

BACKGROUND OF THE INVENTION

This invention relates to endoscopes and endoscopic surgical procedures. More particularly, this invention relates to a device and an associated method for promoting cleanliness in endoscopic surgery. Even more particularly, this invention relates to a liner for an endoscope and an associated surgical technique.

Endoscopes are surgical instruments which enable a relatively non-intrusive visual inspection of and surgery on internal body tissues, particularly including body tissues located within the digestive tract. An endoscope includes a long flexible tubular member which is inserted into the colon through the anus or into the esophagus through the mouth or the nose.

The tubular insertion member of an endoscope generally includes optical fibers for carrying light energy into the patient and for carrying organized visual information out of the patient. The insertion member also includes an elongate cylindrical channel for inserting a surgical instrument into the patient.

The operating tip of a surgical instrument which is inserted through the ancillary, biopsy, channel of an endoscope is controlled by a surgeon who manipulates an actuator at the proximal end of the endoscope. The operation is visually monitored via the visual feedback information provided by the endoscope. Larger endoscopes, particularly for use in the colon, may contain several ancillary channels, e.g., for applying suction and for feeding water and/or air to the distal end of the endoscope's insertion member.

Because endoscopes are expensive instruments, they are used on multiple patients and must accordingly be cleaned after each procedure. Cleaning generally entails soaking at least the distal end of the endoscope's insertion member in an antibacterial and antiviral solution. In addition, the operating channels of the insertion member are flushed, preferably with an antimicrobial cleaning solution.

Such cleaning procedures require substantial amounts of time. Costs are increased, not only because of the hospital personnel time involved, but also because the endoscopes are out of use for that additional time.

Moreover, there is always the risk that the cleaning is inadequate and that dangerous bacteria or viruses remaining in the endoscope may be subsequently transferred to a patient. This risk cannot be ignored in the present environment of AIDS and other dreaded diseases.

It is of further note that a major difficulty in performing endoscopic surgery is that the size of the endoscope's insertion member and consequently the number of instrument or operating channels therein is severely limited by the internal anatomy of the patient. The smaller passages in the gastrointestinal tract form blocks which in some cases must be forcibly dilated to enable passage of the endoscope. Such forcible entry causes trauma or pain to patient.

OBJECTS OF THE INVENTION

An object of the present invention is to provide a device and a related method for promoting cleanliness in endoscopic surgery.

Another object of the present invention is to provide such a device and related method which reduce the time spent on procedures to clean endoscopes.

Another, more particular, object of the present invention is to provide such a device and related method which are easy to use.

A further particular object of the present invention is to provide such a device which is simple and relatively inexpensive to manufacture.

Yet a further object of the present invention is to provide an improved endoscopic surgical procedure which facilitates the introduction of surgical instruments into a patient.

These and other objects of the present invention will be apparent from the drawings and the detailed descriptions herein.

BRIEF DESCRIPTION

A method for preparing an endoscope for an endoscopic surgical operation utilizes, in accordance with the preset invention, a tubular liner element and an endoscope having an insertion member with a biopsy channel extending between a distal end of the insertion member and a proximal end thereof. The method includes inserting the liner element into the biopsy channel from one end thereof, and attaching a distal end of the liner element to the insertion member at least at the distal end thereof.

Preferably, the liner element is flexibly semi-rigid, thereby enabling a pushing of the liner element into the biopsy channel of the endoscope insertion member. The liner element may be inserted either from the proximal end or the distal end of the insertion member. The attachment of the distal end of the liner element to the distal end of the insertion member may be implemented by a collar at the distal end of the insertion member or by a hollow plug inserted into the biopsy channel at the distal end thereof. Most preferably, however, the distal end of the liner element is attached to a distal end of a tubular sheath, and the method further comprises disposing the sheath about the insertion member to enclose at least a distal end portion of the insertion member in a fluid tight seal inside the sheath, the liner element being attached to the insertion member via the sheath.

In accordance with one embodiment of the present invention, the sheath is initially in an inside-out configuration so that the liner element projects free of the liner element. The disposing of the sheath about the insertion member then includes inverting the sheath, the inverting proceeding from the distal end of the insertion member towards the proximal end thereof. In this embodiment of the invention, the disposition of the sheath about the insertion member of the endoscope proceeds only after the liner element has been inserted into the scope's biopsy channel. The inverting of the sheath may be accomplished easily by pushing a ring along the endoscope insertion member, the ring being slidably disposed about the insertion member and between overlapping portions of the sheath.

In one embodiment of the present invention, the liner element is attached to the sheath via a substantially transparent end cap which covers a distal end face of the insertion member upon the inserting of the liner element into the biopsy channel and upon disposing of the sheath about the insertion member. In using the endoscope protected by the liner element and the sheath, optics of the insertion member are utilized to view internal tissues of a patient via the end cap.

A rubber band may be disposed about the sheath on the endoscope insertion member to thereby clamp the sheath to the insertion member.

In a preferred embodiment of the invention, the sheath is provided with a pair of cooperating zip-lock elements, the zip lock elements being separate or spaced from one another during the disposing of the sheath about the insertion member. The method the additionally comprises the mating of the zip-lock elements to one another upon the closure of the distal end portion of the insertion member inside the sheath, thereby locking the sheath about the insertion member. Such a zip-lock sheath is disclosed in U.S. Pat. No. 5,217,001, which is incorporated by reference into this application.

The sheath may be provided with an ancillary tube which defines an elongate channel extending longitudinally alongside a main chamber defined by the sheath. In that case, the method further comprises (a) inserting the insertion member with the liner element attached thereto into a patient, (b) utilizing optics of the endoscope to locate a surgical site inside the patient, (c) upon the locating of the surgical site and prior to a withdrawal of the insertion member from the patient, inserting a surgical instrument having an elongate shaft into the elongate channel and sliding the shaft along the elongate channel so that an operating tip of the surgical instrument protrudes from the elongate channel at the distal end of the insertion member, and (d) performing a surgical operation at the surgical site with the surgical instrument.

In accordance with another embodiment of the present invention, the distal end of the liner element is attached to the sheath only after the sheath has been disposed about the insertion member. The attaching of the liner element to the sheath then includes fastening a rubber band about the sheath and about the distal end of the liner element and thereafter severing a distal end portion of the liner element and a distal tip of the sheath so that a lumen of the liner element is accessible from the distal end of the liner element.

It is alternatively possible for the liner element to be made of substantially flexible film material. in that event, the inserting of the liner element into the biopsy channel includes (i) inserting an elongate rod member through the biopsy channel from one end of the insertion member, (ii) upon an emergence of a tip of the rod member from the biopsy channel, coupling a first end of the liner to the rod member, (iii) upon completion of the step of coupling, pulling the rod member and the first end of the liner through the biopsy channel, (iv) maintaining a second end of the liner outside of the biopsy channel outside of the insertion member during the step of pulling, and (v) upon an emergence of the first end of the liner from the biopsy channel, attaching the second end to the insertion member at the distal end thereof.

A device utilizable with an endoscope to promote cleanliness comprises, in accordance with the invention, a substantially thin-walled elongate tubular sheath made of a flexible material, the sheath having a use configuration with an inner diameter larger than an outer diameter of an insertion member of the endoscope, whereby the sheath may be removably disposed about such insertion member to substantially surround same prior to insertion of the insertion member into a patient. The device further comprises a liner element extending parallel to the sheath inside the sheath at least along a distal end portion of the liner element, the liner element and the sheath being attached to one another at distal ends thereof, the liner element being insertable into a biopsy channel of the insertion member of the endoscope to provide a microbe-tight seal.

In accordance with a feature of the present invention, a securing element is provided on the sheath for facilitating attachment thereof in a fluid tight seal to the insertion member of the endoscope and for concomitantly facilitating subsequent removal of the sheath from the insertion member of the endoscope. The securing element preferably comprises at least one pair of cooperating zip-lock elements extending longitudinally along the sheath.

An endoscope liner in accordance with the present invention is easily applied to the insertion member of an endoscope and is relatively simple to manufacture. By enhancing sanitary conditions in endoscopic procedures, the use of an endoscopic liner in accordance with the present invention exposes patients to a smaller risk of infection. Decreased reliance on complicated postoperative cleaning techniques will reduce non-operation handling of the endoscope, helping to prevent needless wear and tear and extending the useful life of the endoscope.

BRIEF DESCRIPTION OF THE DRAWINGS

FIG. 1 is a schematic perspective view, on a foreshortened scale of an endoscope biopsy channel liner in accordance with the present invention.

FIGS. 2A and 2B are schematic side perspective views of an endoscope showing successive stages in the insertion, into the biopsy channel of the endoscope, of a liner in accordance with the present invention.

FIG. 12 is a schematic cross-sectional view of a biopsy channel liner and sheath assembly in accordance with the present invention, showing the sheath in an inside-out configuration.

FIGS. 13 and 14 are schematic perspective views showing successive steps in the application of the liner and sheath assembly of FIG. 12 to an endoscope insertion member in a method in accordance with the present invention.

FIG. 15 is a partial cross-sectional view, on an enlarged scale, of the liner and sheath assembly of FIG. 12, showing a mode of attachment of the sheath to a lens cap and showing the sheath in a normal use configuration, surrounding the liner element.

5

FIGS. 16 and 17 are schematic perspective views showing successive steps in the application of another liner and sheath assembly to an endoscope insertion member in a method in accordance with the present invention.

FIG. 18 is a schematic perspective view of a proximal end of a liner element of the liner and sheath assembly of FIGS. 17 and 18, showing a plug inserted into the liner element.

Figure 19:
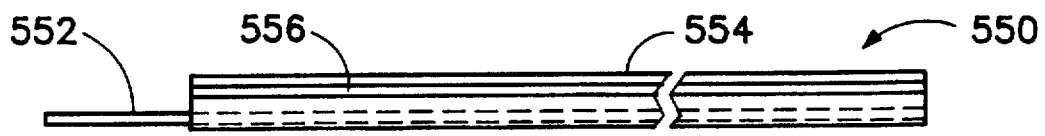

FIG. 19 is a schematic side elevational view of another liner and sheath assembly in accordance with the present invention.

Figure 20:
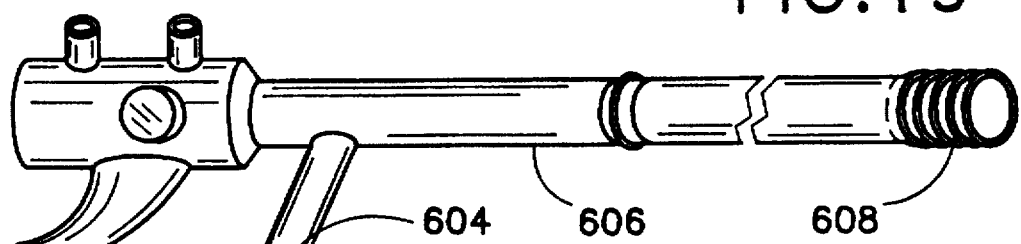
Figure 21:
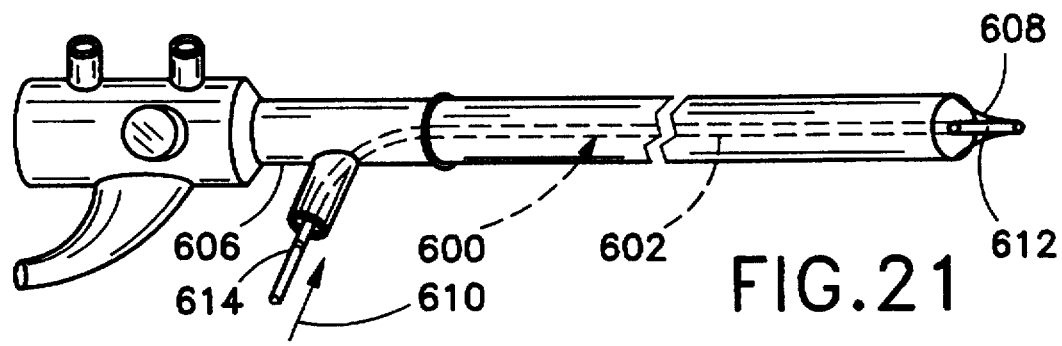

FIGS. 20 and 21 are schematic perspective views showing successive steps in the application of yet another liner and sheath assembly to an endoscope insertion member in a method in accordance with the present invention.

FIGS. 22–25 are partial schematic perspective views, on a larger scale, showing further steps in the method of FIGS. 20 and 21.

DETAILED DESCRIPTION

As illustrated in FIG. 1, a device 10 for lining a biopsy channel of an endoscope comprises a substantially thin walled tubular liner 12 made of a strong, flexible polymeric material. Prior to utilization, liner 10 is in a partially rolled-up collapsed configuration (see FIG. 2A) which facilitates storage thereof.

Figure 3:
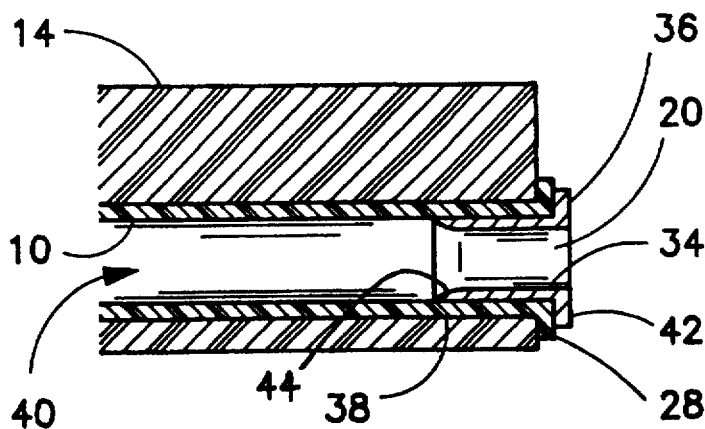
FIG. 3 is a schematic cross-sectional view of a distal end portion of an endoscope insertion member, showing the attachment of a biopsy channel liner to the insertion member.

As shown in FIG. 2A, an endoscope 16 includes an elongate insertion member 14 provided with a biopsy channel (40 in FIGS. 3 and 4) having a proximal opening 18 and a distal opening 20 and forming a passage essentially throughout the length of insertion member 14. In applying liner device 10 to endoscope 16, one inserts an elongate rod member such as a laparoscopic grasper 22 through proximal opening 18 along the biopsy channel until jaws 24 of grasper 22 emerge at distal opening 20. Grasper 22 is then operated to couple a free end 26 of liner 10 to jaws 24 of grasper 22. Grasper 22 is subsequently pulled in a proximal direction through the endoscope biopsy channel to thereby pull free end 26 of liner 10 through the length of insertion member 14. Liner 10 is selected to have a length greater than the length of the biopsy channel (between proximal opening 18 and distal opening 20), so a distal end portion 28 of liner 10 remains outside endoscope insertion member 14 after free end 26 emerges from proximal opening 18 (FIG. 2B). Free end 26 of liner 10 is stretched back over a port stem 30 on insertion member 14 and is fastened thereto by a rubber band 32.

Distal end portion 28 of liner 10 (FIG. 3) is attached to insertion member 14 at a distal end thereof by a collar 36 inserted into distal opening 20 of biopsy channel 40 of insertion member 14. Collar 36 has an outer diameter substantially equal to the inner diameter of biopsy channel 40, so the insertion of collar 36 serves to wedge liner 10 against inner wall 38 of biopsy channel 40, thus forming a seal which prevents the passage of fluids and contaminants around liner 10. Collar 36 is provided with a passage 34 therethrough so as not to block distal opening 20. Collar 36 is further provided with a flange 42 larger in diameter than distal opening 20 to prevent collar 36 from slipping entirely into biopsy channel 40 and to enhance the seal around liner 10. The proximal end 44 of collar 36 is beveled in order to guide surgical instruments inserted through biopsy channel 40 smoothly through passage 34 of collar 36. It is to be noted that collar 36 may be a separate component from liner 10, or it may be permanently secured to liner 10 by an adhesive or welding process. Alternatively, collar 36 may be integral with liner 10.

6

Figure 4:
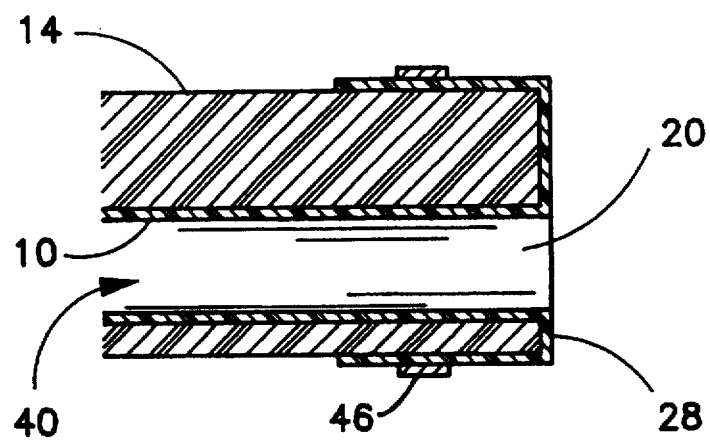
FIG. 4 is a schematic cross-sectional view of the distal end portion of an endoscope, showing another attachment of a biopsy channel liner to the endoscope.
Figure 11:
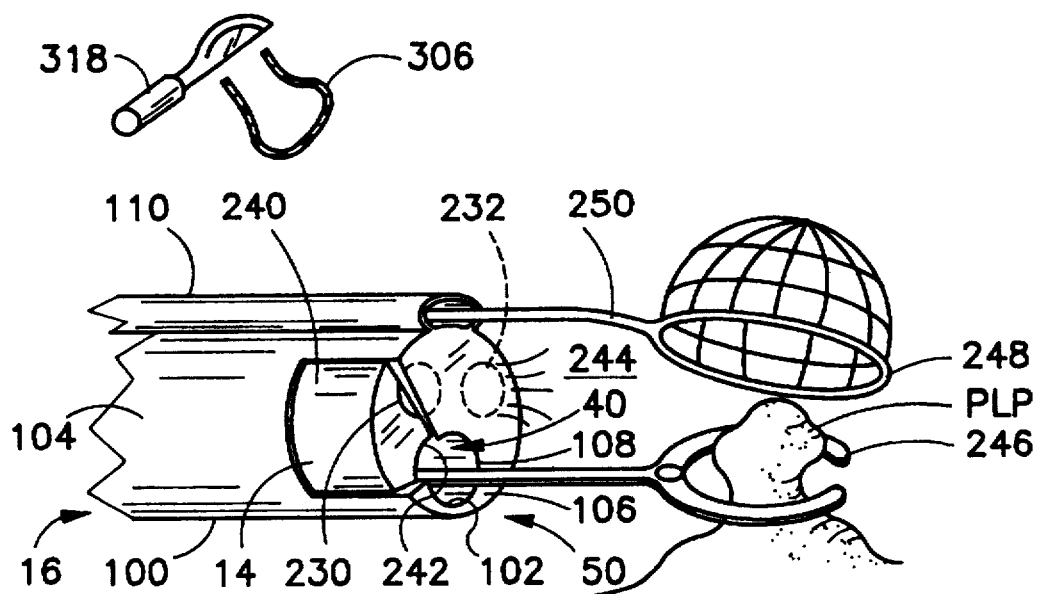
FIG. 11 is a schematic cutaway perspective view of an endoscope with a sheath assembly employed in a surgical procedure in accordance with the present invention.

An alternative method for securing distal end portion 28 of liner 10 to insertion member 14 is illustrated in FIG. 4. Distal end portion 28 is pulled back over insertion member 14 and is secured by a rubber band or other locking ring 46. Distal end portion 28 is transparent to allow light to pass into and out of an image guide 232 and a light guide 234 (FIG. 11). Where distal end portion 28 forms a tubular extension of liner 10 that fits securely and elastically around insertion member 14, rubber band 46 may be omitted.

Figure 5:
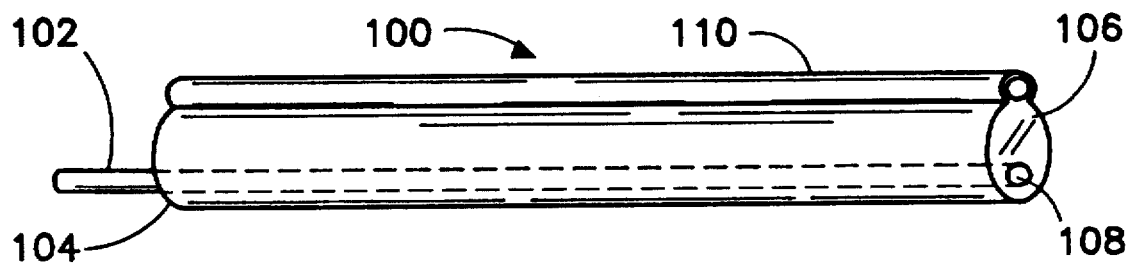
FIG. 5 is a schematic side perspective view of an endoscope sheath assembly in accordance with the present invention.

As illustrated in FIG. 5, a sheath assembly 100 utilizable with an endoscope for promoting cleanliness comprises a tubular polymeric liner 102 insertable into the biopsy channel of an endoscope. A flexible tubular sheath 104 disposable around an endoscope insertion member surrounds liner 102 along at least a portion thereof. Liner 102 and sheath 104 are connected at their distal ends by a transparent cap member 106. Transparent member 106 is provided with an opening 108 to allow access to a channel defined by tubular liner 102. Transparent member 106 forms a seal with liner 102 and sheath 104 to prevent the passage of fluid and contaminants.

As further illustrated in FIG. 5, assembly 100 is also provided with an ancillary tube 110 attached to or integral with sheath 104 along the length thereof. Ancillary tube 110 can be used, for example, for the insertion of surgical instruments or for the supply of water or of suction to a surgical site.

Figure 6:
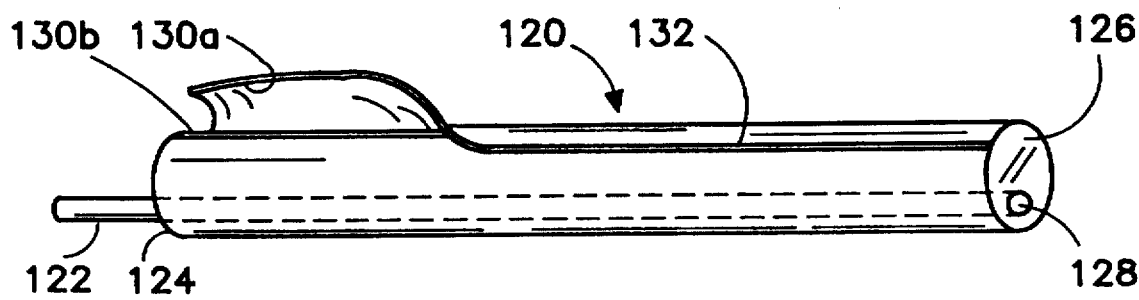
FIG. 6 is a schematic side perspective view of another endoscope sheath assembly in accordance with the present invention.

As shown in FIG. 6, another sheath assembly 120 comprises a tubular liner 122 insertable inside an endoscope biopsy channel and surrounded along at least part of its length by a tubular sheath 124 disposable around an endoscopic insertion member. Liner 122 and sheath 124 are attached to one another at their distal ends by a transparent cap member 126 provided with an opening 128 communicating with liner 122. A slit 132 extends along the length of sheath 124. Slit 132 is alternately sealable and releasable by cooperating zip-lock type elements 130a and 130b extending on either side of slit 132.

Figure 7A:
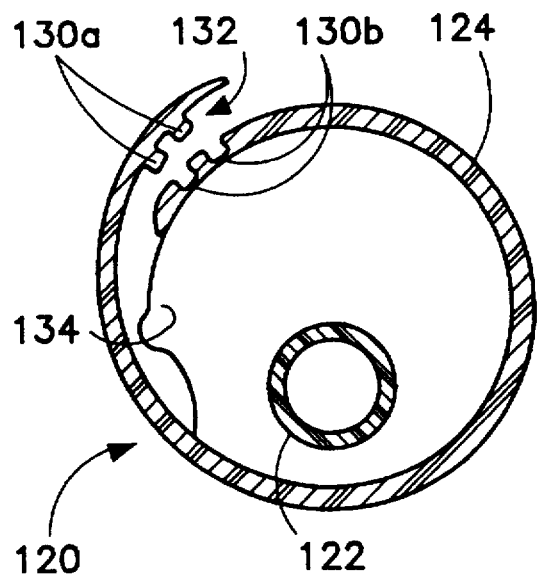
FIGS. 7A–7B are cross-sectional views of an endoscope sheath assembly during successive stages of application of the assembly to the insertion member of an endoscope.
Figure 7B:
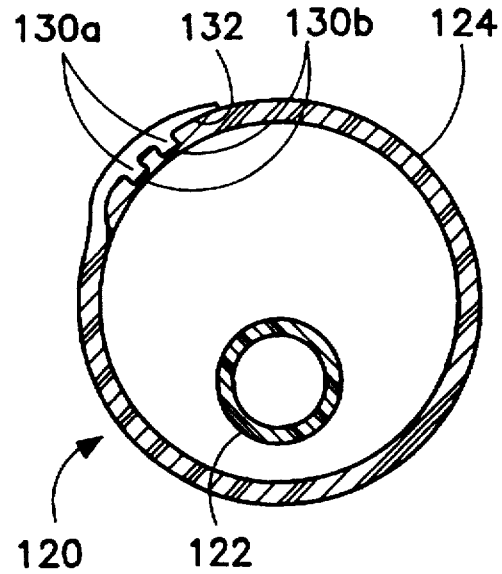

FIG. 7A shows slit 132 in a released or separated configuration. Zip-lock elements 130a are in the form of ribs inserted into respective groove type zip-lock elements 130b. In the released configuration, an endoscope insertion member can easily be slid inside sheath 124, while liner 122 is inserted into an endoscope biopsy channel by a process similar to that shown in FIGS. 2A–2B. An elongate membrane 134 traverses slit 132 along the length thereof to define a closed cylindrical chamber. Once an endoscope insertion member is disposed within sheath 124, rib elements 130a are mated with groove elements 130b to form a sealed configuration shown in FIG. 7B. In the sealed configuration, sheath 124 is held by interlocking zip-lock elements 130a and 130b tightly around the endoscope insertion member. The use of a zip-lock type seal for an endoscopic sheath to facilitate the disposing of the sheath around the insertion member of an endoscope is disclosed in U.S. Pat. No. 5,217,001 to Nakao et al., incorporated herein by reference.

Of course, sheath assembly 120 may be further provided with an ancillary tube similar to ancillary tube 110.

Figure 8:
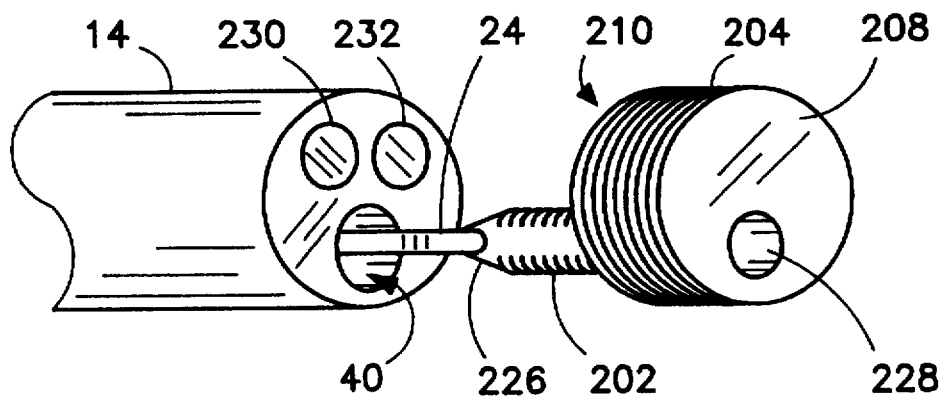
FIG. 8 is a side perspective view of the distal end of an endoscope, showing a stage in the application of an endoscope sheath assembly to the endoscope, in accordance with the present invention.
Figure 9:
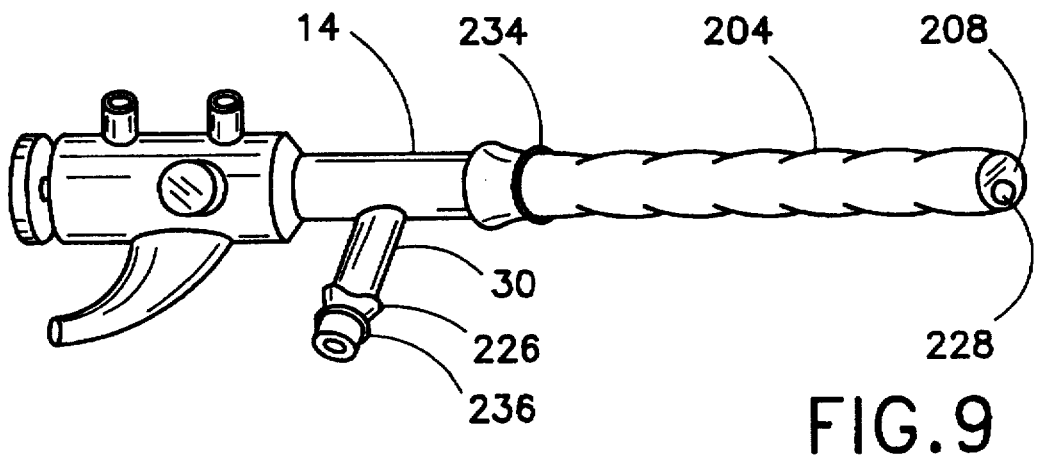
FIG. 9 is a side perspective view of an endoscope sheath assembly attached to an endoscope in accordance with the present invention.

FIG. 8 illustrates a stage in the application of an endoscope sheath assembly 210 to endoscope insertion member 14. Sheath assembly 210 is shown in a partially longitudinally collapsed storage configuration. Jaws 24 of laparoscopic grasper 22 (FIG. 2A) grasp a proximal end 226 of a tubular biopsy channel liner 202 which is surrounded by a sheath 204. Liner 202 and sheath 204 are attached to one another at their distal ends by a transparent cap member 208 having an opening 228 communicating with liner 202. In a procedure analogous to that of FIGS. 2A–2B, a proximal end 226 of liner 202 is pulled by grasper jaws 24 through biopsy channel 40 of insertion member 14. Sheath 204 is then slid over at least a portion of insertion member 14, and transparent cap member 208 is positioned directly over image guide 230 and light guide 232. In the case that sheath 204 covers only a distal segment of insertion member 14, sheath 204 can be sealed to insertion member 14 by its own elasticity or by an elastic band to form the configuration of FIG. 4.

Where sheath 204 covers a substantial portion of insertion member 14, sheath 204 is held tightly to insertion member 14 by its own elasticity or, where sheath 204 is larger in diameter than insertion member 14, by one or more rubber bands or other locking rings 234 (FIG. 9). In addition, proximal end 226 of liner 202 is secured to stem 30 by a rubber band or locking ring 236.

Figure 10A:
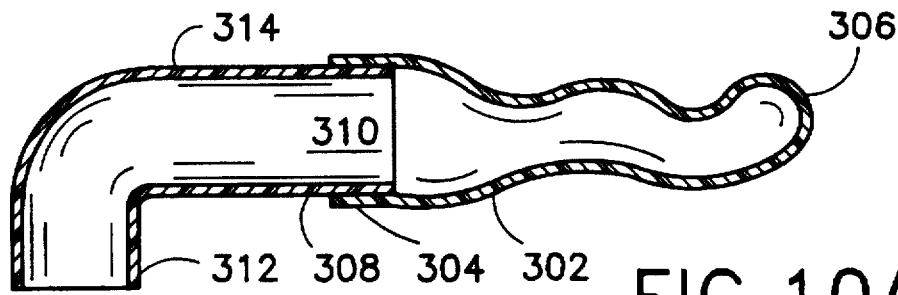
FIGS. 10A–C are schematic cross-sectional views of an endoscope showing successive stages in the application or installation of a biopsy channel liner, in accordance with the present invention.
Figure 10B:
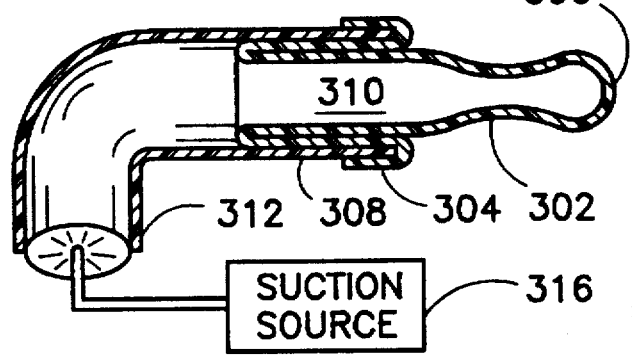
Figure 10C:
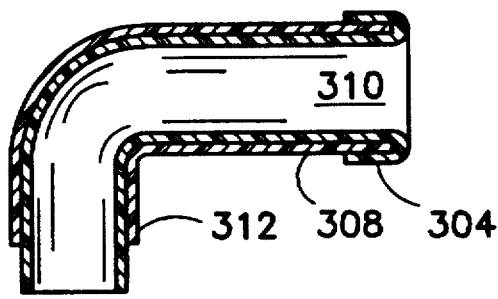

In another endoscope protection method, shown in FIGS. 10A–C, a tubular polymeric liner 302 having an open end 304 and a closed end 306 is attached to a distal end 308 of an endoscopic insertion member 314. Open end 304 can be attached to distal end 308 by any of the methods discussed above. A suction source 316 is applied to a proximal opening 312 of biopsy channel 310. Suction source 316 draws liner 304 into biopsy channel 310, turning it inside-out. When closed end 306 reaches proximal opening 312, suction source 316 is removed, and closed end 306 is severed by a scissors or a scalpel 318. The suction may be applied by a tubular member (not shown) inserted through biopsy channel 310, the distal end of the tubular suction member engaging the inner side of liner closed end 306 in a vacuum lock. Alternatively, a graspers (not shown) may be inserted through biopsy channel 310 to grasp the inner side of liner closed end 306 and subsequently pull liner 302 through the biopsy channel.

In a surgical procedure (FIG. 11), sheath assembly 100 is used with endoscope 16. Sheath assembly 100 is applied to endoscope insertion member 14 prior to insertion into a patient. Insertion member 14 is inserted into the patient before a surgical instrument 250 having an elongated shaft is inserted through ancillary tube 110. This allows ancillary tube 110 to collapse as insertion member 14 passes through narrow passages in the body of the patient, thereby minimizing trauma to the patient. After insertion member 14 is introduced into the patient's body and distal end 50 is positioned at a surgical site 244, surgical instrument 250 is inserted through ancillary tube 110 until an operating tip of instrument 250, such as cauterization snare 248, extends from distal end 50. A forceps 246 is introduced to surgical site 244 through biopsy channel 40. Light from a light guide 232 passes through transparent cap member 106 to illuminate, for example, a polyp PLP at surgical site 244. An image of surgical site 244 is received through cap member 106 by image guide 230 and is displayed in the operating room. Based on the image of surgical site 244, a surgeon manipulates snare 248, forceps 246, and insertion member 14 to perform an endoscopic surgical procedure.

Contaminants, such as bacteria and viruses, from surgical site 244 are prevented by sheath assembly 100 from coming into contact with a surface 240 of endoscope insertion member 14 or with a surface 242 forming a wall of biopsy channel 40. Endoscope sheath 104, transparent cap member 106, and biopsy channel liner 102 together form a fluid tight, germ-proof seal for endoscope 16. Following the completion of the surgical procedure, insertion member 14 is withdrawn from the patient together with endoscope sheath assembly 100. Sheath assembly 100 is then removed from endoscope 16 and discarded. A new sheath assembly can be used with endoscope 16 in a subsequent surgical procedure, thereby minimizing the chance that the use of a single endoscope with many patients will pose a threat of infection.

Sheath assemblies 100, 120, and 210, as well as biopsy channel liner 10, can be used with an endoscope in any of a number of endoscopic surgical procedures. The various applications of these devices will be readily apparent to those familiar with endoscopic surgery.

As illustrated in FIGS. 12 and 15, a biopsy channel liner and endoscope sheath assembly 400 comprises a flexibly semi-rigid liner element 402 attached at a distal end to a transparent lens cap 404 which is disposable in juxtaposition to the distal end 405 (FIG. 13) of an endoscope insertion member 406. A thin-walled flexible sheath 408 is attached at a distal end along an edge of lens cap 404.

As illustrated in FIG. 15, sheath 408 may be provided at its distal end with a ring-shaped rib 410 which is received in an air tight snap-lock fit in an annular groove 412 in end cap 404. Adhesive which is cured by ultraviolet radiation may be used for sealing rib 410 in groove 412. Alternatively or additionally, the attachment of the distal end of sheath 408 to lens cap 404 may be implemented by an ultrasonic or heat weld.

As further illustrated in FIGS. 12 and 15, lens cap 404 is provided with a hollow pin 414 which is insertable into an irrigation channel 416 (FIG. 13) of endoscope insertion member 406.

Prior to use of liner and sheath assembly 400, sheath 408 is disposed inside-out so that liner element 402 projects away from the sheath, as shown in FIGS. 12 and 13. While endoscope insertion member 406 is hanging vertically from an endoscope handpiece or holder 418 its proximal end, liner element 402 is pushed into a biopsy channel 420 of insertion member 406 from a distal end thereof, as indicated by an arrow 422 in FIG. 13. After an emergence of a proximal end 424 of liner element 402 from biopsy channel 420, as illustrated in FIG. 14, sheath 408 is gradually inverted, starting at its upper or distal end, about insertion member 406. To that end, a free ring 426 disposed initially inside the inverted sheath 408 is pushed about insertion member 406. During a continued sliding of ring 426 upwardly along insertion member 406, ring 426 is disposed between overlapping portions 428 and 430 of sheath 408.

Upon a completed inversion of sheath 408 from its initial inside-out configuration to a configuration where it surrounds at least a distal end portion of insertion member 406 and a distal end portion of liner element 402 inside biopsy channel 420, a lip 432 at the proximal end of the sheath may be disposed inside a circumferential groove 434 provided in endoscope insertion member 406 at the proximal end thereof. Alternatively, ring 426 may clamp sheath 408 to insertion member 406 in groove 434.

As mentioned above, pin 414 is inserted into irrigation channel 416. Pin 414 is preferably made of a rigid material such as metal or alloy. Pin 414 is adequate for providing a microbe-barrier at irrigation channel 416 for most applications. Because fluids (saline, air or other gas) pass only in a distal direction through irrigation channel 416, only the distal end thereof need be covered to provide sufficient protection.

After application of liner and sheath assembly 400, as described above, endoscope insertion member 406 is inserted inside a patient and optical elements 436 of the insertion member are used to view internal tissues. An endoscopic instrument such as a biopsy forceps (not shown)

or a polypectomy snare (not shown) may be inserted into the patient via liner element 402.

After the endoscopic diagnostic investigation or operation, insertion member 406 together with liner and sheath assembly 400 is removed from the patient. The removal of liner and sheath assembly 400 from insertion member 406 proceeds in a series of steps reversed from those described above. Fecal matter and possible contaminants are retained inside sheath 408 as it is inverted back to the original inside-out configuration. A plug element 438 (FIG. 12) is inserted into the proximal end 424 of liner element 402 prior to a pulling of liner element in the distal direction through biopsy channel 420. Plug element 438 blocks contaminated organic matter from leaking from liner element 402 into biopsy channel 420 during the removal of the liner element from the biopsy channel.

As illustrated in FIGS. 16 and 17, another liner and sheath assembly 500 comprises a flexibly semi-rigid liner element 502 attached at a distal end to a transparent lens cap 504 which is disposable in juxtaposition to the distal end 506 of an endoscope insertion member 506. A thin-walled flexible sheath 508 is attached at a distal end along an edge of lens cap 504 as described above with reference to FIG. 15. A slit 510 extends along the length of sheath 508. Slit 510 is alternately sealable and releasable by cooperating zip-lock type elements (not shown) extending on either side of slit 510. The zip-lock elements take the same form as elements 130a and 130b described hereinabove with reference to FIG. 7A.

Prior to use of liner and sheath assembly 500, slit 510 is opened or unzipped. As disclosed in U.S. Pat. No. 5,217,001, which is incorporated by reference into this application, sheath 508 has an elongate membrane 512 which bridges slit 510 along the length thereof to define a closed cylindrical chamber. While endoscope insertion member 506 is hanging vertically from an endoscope handpiece or holder 514 its proximal end, liner element 502 is pushed into the biopsy channel (not designated) of insertion member 506 from a distal end thereof. After an emergence of a proximal end 516 of liner element 502 from the endoscope biopsy channel, as illustrated in FIG. 17, sheath 508 is closed by zipping slit 510 shut, as discussed above with reference to FIGS. 6 et seq. FIG. 17 shows sheath 508 in its use configuration enclosing insertion member 506.

Lens cap 504 may be provided with a proximally projecting hollow pin (not shown), as disclosed above with reference to FIGS. 12–15, for enabling the feeding of irrigation fluid and air to the distal end of insertion member 506. Alternatively, end cap 504 may be solid except for a mouth opening 518 of liner element 502. In this case, fluids may be fed to the distal end of insertion member 506 via liner element 502. To that end, a manifold 520 is attached to proximal end 516 of liner element 502 after proximal end 516 emerges from endoscope insertion member 516. Manifold 520 has branches 522, 524, 526 respectively connectable to a pressurized air supply 528, an irrigant source 530 and a suction source 532. Manifold branches 522,524 and 526 are provided with manually actuatable valves 534, 536, 538.

After application of liner and sheath assembly 500, as described above, endoscope insertion member 506 is inserted inside a patient and optical elements 540 of the insertion member are used to view internal tissues. An endoscopic instrument such as a biopsy forceps (not shown) or a polypectomy snare (not shown) may be inserted into the patient via liner element 502.

After the endoscopic diagnostic investigation or operation, insertion member 506 together with liner and sheath assembly 500 is removed from the patient. The removal of liner and sheath assembly 500 from insertion member 506 proceeds in a series of steps reversed from those described above. A plug element plug 542 (FIG. 18) is inserted into the proximal end 516 of liner element 502 prior to a pulling of liner element in the distal direction through the endoscope biopsy channel. Plug element plug 542 blocks contaminated organic matter from leaking from liner element 502 into the biopsy channel during the removal of the liner element from the biopsy channel.

FIG. 19 shows another liner and sheath assembly 550 having a semi-rigid but flexible catheter-like liner element 552 insertable into the biopsy channel of an endoscope. Assembly 550 is provided with a thin-walled flexible sheath 554 for enclosing an endoscope insertion member in a microbe-tight seal. Sheath 554 is attached at a distal end cap (not shown) to a distal end of liner element 552. Sheath 554 may be provided with a slit, as discussed above with reference to FIGS. 6 et seq. and FIGS. 16–18. Alternatively, sheath 554 may be invertible, as discussed above with reference to FIGS. 12–14. In any event, sheath 554 is provided with longitudinally extending integral tube 556 defining an ancillary channel for delivery of irrigation fluids (water, saline, air, other gas) or for the employment of endoscopic instruments including, but not limited to, biopsy forceps and polypectomy snares.

FIGS. 20–25 depict another liner and sheath assembly 600 which includes a flexible and semi-rigid biopsy channel liner element 602 attached to a sheath member 608 during a preoperative application procedure. Sheath member 608 is disposed about an endoscope insertion member 606, as illustrated in FIG. 20, by sliding, rolling or inverting about insertion member 606. Liner element 602 is then inserted into a biopsy channel 604 of insertion member 606 from a proximal end thereof, as indicated by an arrow 610 in FIG. 21, until a distal end portion 612 of predeterminate length protrudes from the distal end of insertion member 606. To facilitate the protrusion of the proper length of liner element 602, that element is provided at its proximal end with a marker such as a colored band 614.

Figure 22:
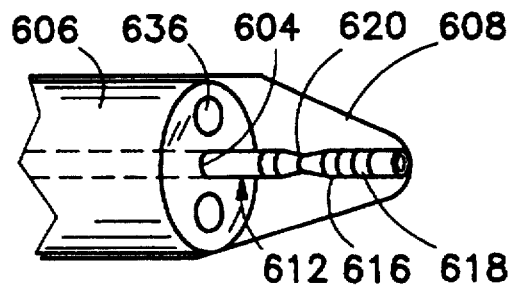
Figure 24:
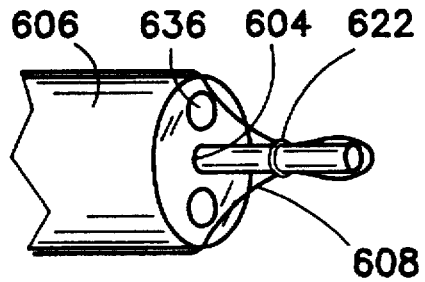
Figure 23:
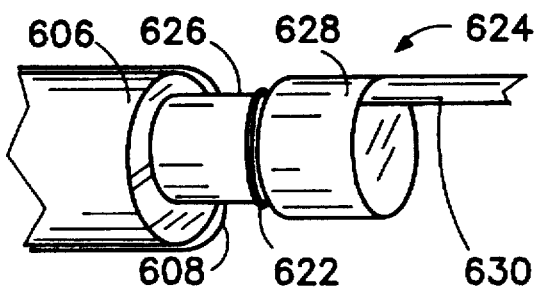

Along distal end portion 612, liner element 602 is provided with two colored bands 616 and 618 (FIG. 22). An annular groove 620 is formed in distal end portion 612 at the proximal band 616 for receiving a rubber band or ring 622 applied via an instrument 624 (FIG. 23). Instrument 624 can be a conventional hemorrhoid ligator which includes an inner cylinder 626 around which rubber band 622 is stretched. Cylinder 626 is telescopingly received into an outer cylinder 628 which, under manipulation by a user via an actuator arm 630, moves over inner cylinder 626 to push rubber band 622 off of the inner cylinder and into groove 620, as shown in FIG. 24.

Figure 25:
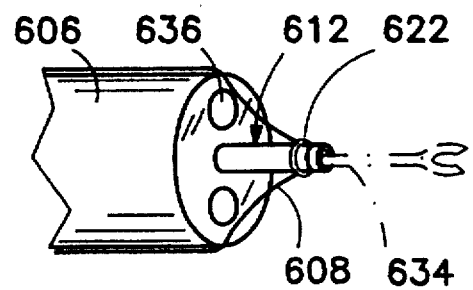

After the snapping of rubber band 622 into groove 620, a scissors or other cutter (not shown) is used to snip off a distal tip of liner element 602 and a distal end portion 632 of sheath 608. The cutting operation may be guided by the distalmost colored band 618 on distal end portion 612 of liner element 602. After the severing of the distal tip of liner element 602 and distal end portion 632 of sheath 608, endoscope insertion member 606 and liner and sheath assembly 600 may be employed inside a patient. Then, an endoscopic diagnostic or surgical instrument 634 is inserted through liner element 602, as shown in FIG. 25.

After the endoscopic diagnostic or surgical procedure is over and insertion member 606 is removed from the patient, a plug like plugs 438 and 542 is inserted into the proximal end of the liner element 602, which is then pulled in the distal direction through the endoscope biopsy channel. Sheath 608 is removed from insertion member 606 by rolling, sliding or inverting (FIGS. 12–14). The extraction of liner element 602 and the removal of sheath 608 can be easily effectuated to prevent microbial contamination of the scope.

It is to be noted with respect to the embodiment of FIGS. 20–25 that sheath 608 is substantially transparent, at least at the distal end thereof. Distal end portion 612, including stripes or bands 616 and 618 must be visible through the sheath. More importantly, optical elements 636 of insertion member 606 must receive light in an undistorted fashion through sheath 608.

It is to be observed that liner element 602 may be alternatively inserted into the endoscope biopsy channel from the distal end of insertion member 606, prior to the disposition of sheath 608 about insertion member 606.

It is to be noted that a biopsy channel liner as described herein need not be sterile for most applications. However, its cleanliness should conform to prevailing medical standards.

Although the invention has been described in terms of particular embodiments and applications, one of ordinary skill in the art, in light of this teaching, can generate additional embodiments and modifications without departing from the spirit of or exceeding the scope of the present invention. Accordingly, it is to be understood that the drawings and descriptions herein are preferred by way of example to facilitate comprehension of the invention and should not be construed to limit the scope thereof.

What is claimed is:

1. A method for preparing an endoscope for an endoscope surgical operation, comprising:
providing an endoscope having an insertion member with a biopsy channel extending between a distal end of said insertion member and a proximal end thereof;
also providing a tubular liner element having a distal end attached to a distal end of a tubular sheath, said sheath being initially in an inside-out configuration so that said liner element projects free of said sheath;
disposing said sheath about said insertion member to enclose at least a distal end portion of said insertion member in a fluid tight seal inside said sheath, the disposing of said sheath about said insertion member including inverting said sheath, said inverting proceeding from the distal end of said insertion member towards the proximal end thereof;
inserting said liner element into said biopsy channel from one end thereof; and
attaching said distal end of said liner element to said insertion member at least at the distal end thereof, said liner element being attached to said insertion member via said sheath.

2. The method defined in claim 1 wherein the inverting of said sheath includes pushing a ring slidably disposed about said insertion member and between overlapping portions of the sheath.

3. The method defined in claim 1 wherein said liner element is attached to said sheath via a substantially transparent end cap which covers a distal end face of said insertion member upon the inserting of said liner element into said biopsy channel and upon disposing of said sheath about said insertion member, further comprising utilizing optics of said insertion member to view internal tissues of a patient via said end cap.

4. The method defined in claim 3 wherein said end cap includes a hollow pin projecting in a proximal direction from said end cap, further comprising inserting said pin into an irrigation channel of said insertion member, said irrigation channel being separate from said biopsy channel.

5. The method defined in claim 1, further comprising attaching at least one rubber band about said sheath upon enclosing said distal end portion of said insertion member inside said sheath, thereby clamping said sheath to said insertion member.

6. The method defined in claim 1 wherein said sheath is provided with a pair of cooperating zip-lock elements, said zip lock elements being separate or spaced from one another during the disposing of said sheath about said insertion member, also comprising mating said zip-lock elements to one another upon enclosing said distal end portion of said insertion member inside said sheath, thereby locking said sheath about said insertion member.

7. The method defined in claim 1 wherein said sheath has an ancillary tube which defines an elongate channel extending longitudinally alongside a main chamber defined by said sheath, further comprising:
inserting said insertion member with said liner element attached thereto into a patient;
utilizing optics of said endoscope to locate a surgical site inside the patient;
upon the locating of the surgical site and prior to a withdrawal of said insertion member from the patient, inserting a surgical instrument having an elongate shaft into said elongate channel and sliding said shaft along said elongate channel so that an operating tip of said surgical instrument protrudes from said elongate channel at the distal end of said insertion member;
performing a surgical operation at said surgical site with said surgical instrument.

8. The method defined in claim 1 wherein said liner element is flexibly semi-rigid, the inserting of said liner element into said biopsy channel including the pushing of said liner element into said biopsy channel.

9. A method for preparing an endoscope for an endoscopic surgical operation, comprising:
providing an endoscope having an insertion member with a biopsy channel extending between a distal end of said insertion member and a proximal end thereof;
also providing a tubular liner element;
inserting said liner element into said biopsy channel from one end thereof;
attaching a distal end of said liner element to said insertion member at least at the distal end thereof
disposing a sheath about said insertion member to enclose at least a distal end portion of said insertion member in a fluid tight seal inside said sheath; and
attaching the distal end of said liner element to said sheath after the sheath has been disposed about said insertion member.

10. The method defined in claim 9 wherein the attaching of said liner element to the sheath includes:
fastening a rubber band about said sheath and about the distal end of said liner element; and
after the fastening of said rubber band, severing a distal end portion of said liner element and a distal tip of said sheath so that a lumen of said liner element is accessible from the distal end of said liner element.

11. A method for preparing an endoscope for an endoscopic surgical operation, comprising:

providing an endoscope having an insertion member with a biopsy channel extending between a distal end of said insertion member and a proximal end thereof;

also providing a tubular liner element;

inserting said liner element into said biopsy channel from one end thereof; and attaching a distal end of said liner element to said insertion member at least at the distal end thereof, said liner element being made of substantially flexible film material, the inserting of said liner element into said biopsy channel including:

inserting an elongate rod member through said biopsy channel from one end of said insertion member;

upon an emergence of a tip of said rod member from said biopsy channel, coupling a first end of said liner element to said rod member;

upon completion of the coupling of the first end of said liner element to said rod member, pulling said rod member and said first end of said liner element through said biopsy channel;

maintaining a second end of said liner element outside of said biopsy channel during the pulling of the rod member and the first end of the liner element; and upon an emergence of said first end of said liner element from said biopsy channel, attaching said second end to said insertion member at the distal end thereof.

12. The method defined in claim 11 wherein said liner element is in a collapsed configuration prior to the coupling of the first end of said liner element to said rod member, further comprising unfurling said liner element from said collapsed configuration during said step of pulling.

13. The method defined in claim 11 wherein said liner element is provided at its distal end with a collar element having an outer diameter substantially equal to a diameter of said biopsy channel, the attaching of the distal end of the liner element to the insertion member including force fitting said collar element into said biopsy channel at the distal end of said insertion member.

* * * * *